United States Patent [19]

Chiba et al.

[11] Patent Number: 4,917,885

[45] Date of Patent: Apr. 17, 1990

[54] HARD MEDICINAL CAPSULE

[75] Inventors: Tohru Chiba; Hiroaki Muto; Soji Tanioka; Yuichi Nishiyama, all of Niigata; Noboru Hoshi; Yoshiro Onda, both of Tokyo, all of Japan

[73] Assignee: Shin-Etsu Chemical Co., Ltd., Tokyo, Japan

[21] Appl. No.: 946,119

[22] Filed: Dec. 23, 1986

Related U.S. Application Data

[63] Continuation of Ser. No. 734,289, May 15, 1985.

[30] Foreign Application Priority Data

Oct. 23, 1984 [JP] Japan .................................. 59-222676

[51] Int. Cl.$^4$ ............................................. A61K 31/74
[52] U.S. Cl. ........................................................ 424/78
[58] Field of Search ............................................ 424/78

[56] References Cited

U.S. PATENT DOCUMENTS 4,388,442  6/1983  Taniguchi et al. ................... 524/297

OTHER PUBLICATIONS

Chemical Abstracts, vol. 78 (1973), #2D183A; Okusa et al.

*Primary Examiner*—Joseph A. Lipovsky
*Attorney, Agent, or Firm*—Jules E. Goldberg

[57] ABSTRACT

In place of gelatin conventionally used as a material for shaping hard medicinal capsules, the invention proposes a hard capsule for medicinal use shaped of a polymer blend of a water-soluble cellulose ether, e.g., alkyl cellulose, hydroxyalkyl cellulose and alkyl hydroxyalkyl cellulose, and a polyvinyl alcohol in a weight ratio of 70:30 to 98:2. The inventive hard medicinal capsules have remarkably low permeability to oxygen and moisture with little influences on the medicament contained therein along with sufficiently high mechanical strengths and are much more stable than conventional gelatin-made capsules against the influences of the ambient conditions, such as, the crack formation unavoidable in a gelatin-made hard capsule when it is kept under an extremely low humidity.

10 Claims, No Drawings

HARD MEDICINAL CAPSULE

This is a continuation of application Ser. No. 734,289, filed May 15, 1985.

BACKGROUND OF THE INVENTION

The present invention relates to a hard medicinal capsule shaped of a novel polymeric composition as well as to a method for shaping such a hard capsule formed of the polymeric composition.

As is well known, the most widely used material of hard medicinal capsules in the prior art is gelatin and a hard medicinal capsule of gelatin is prepared usually in a process in which a mandrel pin is dipped in a bath of an aqueous solution of gelatin followed by withdrawing of the pin out of the solution and drying of the solution on the pin to form a crust of gelatin and the mandrel pin is pulled away from the gelatin crust which is then trimmed into a finished form.

Gelatin-made hard medicinal capsules prepared in this manner, however, have several problems and disadvantages, for example, that gelatin is a proteinaceous material with reactivity so that certain medicament ingredients contained in a gelatin capsule may interact with gelatin and be denatured, that a gelatin capsule prolongedly kept under an extremely low humidity may become brittle and sometimes is broken in handling while, when a gelatin-made medicinal capsule is kept under a highly humid condition, the medicament ingredient may sometimes be denatured due to the increased moisture inside the capsule and that gelatin is liable to the attack of microorganisms so that the quality of a gelatin-made hard capsule is unavoidably degraded in the lapse of time.

With an object to overcome the above mentioned problems and disadvantages of gelatin-made hard medicinal capsules, proposals and attempts have been made to shape a hard medicinal capsule of a material other than gelatin. For example, cellulose ethers with alkyl or hydroxyalkyl groups as the substituents on the cellulose molecules are proposed in the form of an aqueous or organic solution as a substitute of the aqueous solution of gelatin for the preparation of hard medicinal capsules. These cellulose derivatives, however, are not quite satisfactory as a material of medicinal capsules due to the relatively large permeability of the capsule walls made thereof to oxygen and moisture resulting in the denaturation of the medicament ingredients contained in the capsule. Other materials hitherto proposed as a base of hard medicinal capsules include starch, α-starch, hydroxyalkyl starch, sodium alginate, sodium salt of a copolymer of gelatin and acrylic acid and the like although hard capsules made of these materials are hardly applicable to practical use due to the low mechanical strength of the capsule and possible reactivity of the capsule walls with the medicament ingredients as a consequence of the ionic nature of the material.

SUMMARY OF THE INVENTION

It is therefore an object of the present invention to provide a hard medicinal capsule made of a material free from the above described problems and disadvantages in the conventional materials of hard capsules including not only gelatin but also other substitute materials for gelatin.

Thus, the hard medicinal capsule provided as a result of the extensive investigations undertaken with the above mentioned object is made of a polymeric composition comprising from 70 to 98 parts by weight of a cellulose ether, of which the ether-forming substituent groups are selected from the class consisting of alkyl groups and hydroxyalkyl groups and from 30 to 2 parts by weight of a polyvinyl alcohol.

The method of the invention for shaping a hard capsule of the above defined polymeric composition comprises dipping a mandrel pin preheated at a temperature in the range from 45 to 100° C. in an aqueous solution containing the above defined polymeric composition dissolved therein, withdrawing the mandrel pin out of the solution, drying the aqueous solution on the surface of the mandrel pin to form a dried crust of the polymeric composition and removing the mandrel pin from the thus formed crust of the polymeric composition thereon.

DESCRIPTION OF THE PREFERRED EMBODIMENTS

DETAILED

The hard medicinal capsule of the invention made of the above described unique polymeric composition as the base material has several advantages over those made of a conventional capsule material such as gelatin and the like, for example, that the capsule gains no brittleness even when it is prolongedly kept under an extremely low humidity while the increase of moisture inside the capsule is not significant even when the capsule is kept under a highly humid condition to cause little denaturation of the medicament ingredients contained therein, that the component polymers of the base material of the inventive capsule have lower reactivity than gelatin so that the danger of the interaction of the capsule material with the medicament ingredients contained therein is minimized, that the permeability of the capsule walls to oxygen and moisture is much smaller than the capsules shaped of the alkyl- and/or hydroxyalkyl-substituted cellulose ether alone to minimize the denaturation of the medicament ingredients contained in the capsule, that the mechanical strength of the capsule is much higher than the gelatin-made capsules and the capsule is safer against the microbiological contamination and degradation than the gelatin-made capsules, and that the polymeric base material is readily soluble in water to give an aqueous solution having adequate concentration and viscosity from which the capsules are prepared by the method of pin-dipping as in the gelatin-made capsules so that the finished capsules are absolutely free from the safety problem due to the trace amount of an organic solvent remaining in the capsule walls.

One of the components in the polymeric composition as the base material, of which the inventive capsule is shaped, is an alkyl- and/or hydroxyalkyl-substituted cellulose ether or, in other words, a cellulose ether of which the ether-forming substituent groups are selected from the class consisting of alkyl groups and hydroxyalkyl groups. The alkyl groups are typically methyl and ethyl groups and the hydroxyalkyl groups are typically hydroxyethyl and hydroxypropyl groups. Exemplary of suitable cellulose ethers are therefore methyl cellulose, hydroxyethyl cellulose, hydroxypropyl cellulose, hydroxyethyl methyl cellylose, hydroxyethyl ethyl cellulose, hydroxypropyl methyl cellulose and the like. In order to satisfy the requirement in the invention that the cellulose ether should be soluble in water, it is usually preferable that the number of the substituent groups, i.e. alkyl groups and hydroxyalkyl groups, in the cellulose ether is at least 1.4 per glucose unit of the cellulosic structure. Although the degree of polymerization, which is usually specified in terms of the viscosity of an aqueous solution, is not particularly limitative, a 2% by weight aqueous solution of the cellulose ether should preferably have a viscosity in the range from 2 to 15 centipoise at 20° C. When the cellulose ether is more highly polymeric than above, inconveniences are caused in the capsule-shaping works with an aqueous solution thereof unless the concentration of the solution is undesirably decreased.

As is readily understood when the types of the substituent groups, i.e. alkyl and hydroxyalkyl groups, on the cellulose structure are considered, the cellulose ether used in the invention is absolutely non-ionic with little reactivity with most of the medicament ingredients contained in the capsule to be free from the safety problem by the denaturation thereof. In contrast therewith, carboxymethyl cellulose and the like cellulose derivatives are ionic in nature and cannot be used in place of the alkyl- and/or hydroxyalkyl-substituted cellulose ethers used in the invention due to the possible danger of interaction with the medicament ingredients to cause denaturation thereof.

The other essential component of the polymeric composition as the base material of the medicinal capsule of the invention used in combination with the above described cellulose ether is a polyvinyl alcohol. Although the type of the polyvinyl alcohol is not particularly limitative, it is preferably a partially or completely saponified one having a degree of saponification of at least 75%. The degree of polymerization of the polyvinyl alcohol is still less limitative than of the cellulose ether described above since polyvinyl alcohols usually give an aqueous solution of a much lower viscosity than cellulose ethers when the concentrations are the same but the polyvinyl alcohol should preferably have such a degree of polymerization that a 4% by weight aqueous solution thereof has a viscosity in the range from 3 to 80 centipoise at 20° C.

The combined use of a cellulose ether and a polyvinyl alcohol has a synergistic effect on the performance of the hard capsule made of the polymeric mixture thereof. Namely, cellulose ethers in general are excellent in the mechanical strength of a film shaped thereof with small decrease of the strength under an extremely low humidity so that the capsules made thereof are safer against mechanical break than gelatin-made hard capsules while, on the other hand, polyvinyl alcohols have a characteristically low permeability to oxygen and moisture. Therefore, the inventive hard capsules made of the polymeric mixture of these two types of polymers are imparted with the advantageous features inherent in the respective polymers.

The blending ratio of the cellulose ether and the polyvinyl alcohol should be such that the mixture thereof is composed of from 70 to 98% by weight of the cellulose ether and from 30 to 2% by weight of the polyvinyl alcohol. When the amount of the polyvinyl alcohol is smaller than 2% by weight, no significant improvement can be obtained in the permeability of the capsule walls to oxygen and moisture. When the amount of the polyvinyl alcohol is in excess of 30% by weight, on the other hand, mechanical strengths of the hard capsule may be decreased due to the loss of miscibility between the cellulose ether and the polyvinyl alcohol. It is of course that the miscibility between these two polymers can be regained when the amount of the polyvinyl alcohol is increased to such a large extent that the polyvinyl alcohol is the main component of the polymeric mixture but a capsule shaped of such a polymeric mixture no longer has hardness as a hard medicinal capsule due to the appearance of excessive flexibility inherent to polyvinyl alcohols.

In the shaping process of the inventive hard medicinal capsule, an aqueous solution containing a cellulose ether and a polyvinyl alcohol in a desired proportion is first prepared. The overall concentration of the polymers in the aqueous solution should preferably be in the range from 10 to 30% by weight and the aqueous solution should preferably have a viscosity in the range from 1000 to 10,000 centipoise at 20° C. When the concentration and/or the viscosity of the solution are lower than the above ranges, the capsule shaped of such a solution may have no sufficient thickness of the walls while difficulties are encountered in working with an aqueous solution having a polymer concentration and/or a viscosity higher than the above ranges. The aqueous solution is then fully deaerated by being kept standing or brought under a reduced pressure. Into the aqueous solution heated at an appropriate temperature is dipped a mandrel pin heated in advance at a temperature in the range from 45° to 100° C. or, preferably, from 60° to 90° C. and the pin is, after keeping in the solution for a while, withdrawn gradually out of the solution and dried in a drying oven to form a crust-like film of the polymeric blend on the capsule-shaped pin which is then freed from the mandrel pin by pulling out and trimmed to give a body of the capsule. A cap of the capsule having a slightly larger diameter than the body is shaped separately in a similar manner and put on the body containing a medicament to finish a hard medicinal capsule.

In the above described process for shaping a hard capsule by the pin-dipping technique, it is preferable that the mandrel pin is preheated prior to dipping in the solution at a temperature in the above mentioned range. This is because to utilize the very unique viscosity behavior of an aqueous solution of certain cellulose ethers such as alkyl celluloses and hydroxyalkyl alkyl celluloses which, differently from most of solutions of other polymers, becomes gelled at a temperature higher than a critical temperature. Accordingly, dipping of a mandrel pin preheated at a temperature higher than the gelation temperature of the solution in the aqueous solution may readily result in the formation of a relatively thick and uniform layer of the hydrated polymer therearound even when the concentration or viscosity of the solution is relatively low. In contrast therewith, the pin-dipping method for shaping a gelatin-made hard capsule is usually performed without preheating the mandrel pin.

It is of course optional that the polymeric base mixture of the inventive hard capsule is admixed with various kinds of known additives including, for example, plasticizers such as glycerin, sorbitol, mannitol, sucrose, polyethylene glycol and the like, shading agents such as titanium dioxide, barium sulfate, precipitated calcium carbonate and the like, coloring agents such as water-soluble colors, lake pigments and the like, and others. Removal of the mandrel pin from the polymeric crust shaped thereon may be facilitated by coating the surface of the mandrel pin in advance with a mold-release agent such as cottonseed oil and liquid paraffin.

In the following, the hard capsule of the invention is described in more detail by way of examples preceded by a description of a Preliminary Test for the evaluation of several polymeric blends.

Preliminary Test

Several polymeric base materials were shaped each into a film having a thickness of 100 μm by the technique of casting of a solution for the measurements of several properties shown below. The polymers used here include three cellulose ethers, three polyvinyl alcohols and a product of gelatin characterized in the following, in which DS and MS are each the number of the substituent alkyl groups and hydroxyalkyl groups, respectively, per glucose unit in the cellulose ethers and the values of the viscosity are each the value of an aqueous solution containing 2% by weight of the cellulose ether or 4% by weight of the polyvinyl alcohol measured at 20° C.

Cellulose Ethers

Hydroxypropyl methyl cellulose (HPMC): DS=1.88; MS=0.19; and viscosity=5.7 centipoise
Methyl cellulose (MC): DS=1.73; and viscosity=6.4 centipoise
Hydroxyethyl cellulose (HEC): MS=1.80; and viscosity=13.0 centipoise Polyvinyl Alcohols PVA-A: degree of saponification=88.0% by moles; and viscosity=5.0 centipoise.
PVA-B: degree of saponification=88.0% by moles; and viscosity=45.0 centipoise
PVA-C: degree of saponification=98.5% by moles; and viscosity=5.5 centipoise
Gelatin: Type No. G-1094, a product by Nitta Gelatin Co.

Films of 100 μm thickness were shaped of different combinations in different proportions by weight of the cellulose ethers and polyvinyl alcohols as well as the gelatin alone and subjected to the measurements in the manner described below for the respective properties.

Permeability to oxygen: a circular test piece of 3 cm diameter was taken from the film by cutting and the permeability of the test piece to oxygen was determined at 25° C. by use of a gas permeability tester to give the results shown in Table 1.

Permeability to moisture: a circular test piece of 2 cm diameter sandwiched by two silicone rubber sheets of 2 cm diameter provided with a circular center opening of 1 cm diameter was attached to the mouth of a 10 ml glass vial containing a saturated aqueous solution of sodium chloride and covered with an aluminum plate provided with a circular center opening of 1 cm diameter and kept in a desiccator containing anhydrous calcium chloride for 3 days at 20° C. to determine the weight decrease of the sodium chloride solution after 3 days of conditioning at the same temperature to give the results shown in Table 1.

Impact strength: square test pieces of each 3 cm by 3 cm wide taken from the film were, after absolute drying, conditioned for humidity at a temperature of 25° C. in atmospheres of relative humidities of 0%, 32% and 58% and the impact strengths thereof were determined in the following manner by use of a DuPont's impact tester to give the results shown in Table 1.

TABLE 1

| Base material of film | | Oxygen permeability, ml/$m^2$. 24 hours. atom | Moisture permeability. g/$m^2$. 24 hours | Impact strength. mm. under relative humidity of | | |
|---|---|---|---|---|---|---|
| | | | | 0% | 32% | 58% |
| Gelatin | | 5 | 300 | 10 | 28 | 50 |
| HEC:PVA-A | 100:0 | 70 | 340 | — | — | — |
| | 95:5 | 45 | 250 | — | — | — |
| | 90:10 | 31 | 200 | — | — | — |
| | 70:30 | 18 | 150 | — | — | — |
| HPMC:PVA-B | 100:0 | 460 | 360 | — | — | — |
| | 95:5 | 230 | 280 | 43 | 80 | 180 |
| | 90:10 | 160 | 230 | — | — | — |
| | 70:30 | 37 | 180 | 39 | 75 | 170 |
| | 60:40 | — | — | 12 | 18 | 38 |
| HPMC:PVA-C | 95:5 | 210 | 260 | — | — | — |
| | 90:10 | 150 | 210 | — | — | — |
| | 70:30 | 41 | 170 | — | — | — |
| HEC:PVA-C | 95:5 | 50 | 240 | 60 | 85 | 200 |
| | 90:10 | 39 | 190 | — | — | — |
| | 70:30 | 22 | 160 | 55 | 80 | 180 |
| | 60:40 | — | — | 16 | 20 | 40 |

In this instrument, measurement of the impact strength was performed by dropping a weight of 300 g on to the test specimen of the film from varied heights and the height for the 50% break of the test specimens was taken as representing the impact strength when 10 test specimens were tested for each height.

Moisture absorption at equilibrium: a set of 40 square pieces each 1 cm by 1 cm wide taken from the film and weighing about 0.5 g was, after absolute drying, kept standing in an atmosphere of 58%, 75% or 88% relative humidity at 25° C. until equilibrium of moisture absorption had been established and the amount of the weight increase was determined to give the results shown in Table 2.

Ultimate elongation and tensile strength: a #1 dumbbell test specimen taken from the film was, after absolute drying, conditioned for humidity by keeping for 48 hours in an atmosphere of 58% relative humidity at 25° C. and subjected to the tensile test of the ultimate elongation at break and tensile strength by use of an automatic tensile tester at a pulling velocity of 10 mm/minute at a temperature of 20° C. to give the results shown in Table 2.

EXAMPLE 1

An aqueous solution containing 18% by weight of solid matter was prepared by dissolving the same HPMC and PVA-A as used in Preliminary Test described above in a weight proportion of 97:3 and, after standing overnight as such, was deaerated under reduced pressure. The thus prepared aqueous solution for a dipping bath was heated at 40° C. and a mandrel pin for #3 capsule heated in advance at 85° C. was dipped therein and withdrawn therefrom taking 50 seconds immediately followed by drying for 3 minutes in a drying oven at 75° C.

TABLE 2

| Base material of film | | Moisture absorption, %, at equilibrium under relative humidity of | | | Ultimate elongation % | Tensile strength. kg/$cm^2$ |
|---|---|---|---|---|---|---|
| | | 58% | 75% | 88% | | |
| Gelatin | | 17.1 | 22.2 | 36.0 | 10.0 | 875 |
| HPMC:PVA-A | 95:5 | 7.0 | 11.6 | 26.0 | 9.7 | 492 |
| | 80:20 | 6.8 | 11.8 | 25.0 | 10.0 | 475 |

TABLE 2-continued

| Base material of film | | Moisture absorption, %, at equilibrium under relative humidity of | | | Ultimate elongation % | Tensile strength, kg/cm² |
|---|---|---|---|---|---|---|
| | | 58% | 75% | 88% | | |
| | 70:30 | 7.1 | 11.7 | 27.0 | 11.0 | 465 |
| | 30:70 | 7.0 | 11.5 | 27.0 | 62.5 | 390 |
| | 0:100 | 7.1 | 11.8 | 25.0 | 84.5 | 352 |
| MC:PVA-C | 95:5 | 5.8 | 10.8 | 23.5 | 12.0 | — |
| | 80:20 | 6.0 | 11.0 | 24.0 | 12.5 | — |
| | 70:30 | 6.5 | 11.5 | 25.0 | 13.0 | — |
| | 30:70 | 7.0 | 11.5 | 26.5 | 60.5 | — |
| | 0:100 | 7.5 | 12.0 | 26.0 | 75.1 | — |

Drying was further continued for 27 minutes in the same drying oven with reversal to give a crust-like body which was then pulled out of the mandrel pin and trimmed to give a capsule body. A cap of the capsule to fit the body was prepared separately in a similar manner. The capsule body filled with starch as a simulated medicament was capped therewith to give a finished hard capsule which was subjected to the disintegration test in a procedure specified in The Pharmacopoeia of Japan, 10th Edition, to give a result of 6.5 minutes of the disintegration time.

EXAMPLE 2

An aqueous solution as a dipping bath containing 18% by weight of solid matter was prepared in a manner similar to Example 1 by dissolving the same HPMC and PVA-C as used in Preliminary Test described above in water in a weight proportion of 75:25. A hard capsule was prepared of this solution in the same manner as in Example 1 and the capsule was subjected to the disintegration test to give a result of the disintegration time of 7.0 minutes.

EXAMPLE 3

An aqueous dipping bath containing 26% by weight of solid matter was prepared by dissolving in water the same PVA-A as used in Preliminary Test described above, a hydroxyethyl methyl cellulose, of which the numbers of substitution with methyl groups and hydroxyethyl groups per glucose unit were 1.40 and 0.20, respectively, and the viscosity of a 2% by weight aqueous solution was 3.0 centipoise at 20° C., and a methyl cellulose, of which the number of substitution with methyl groups per glucose unit was 1.83 and the viscosity of a 2% by weight aqueous solution was 3.2 centipoise at 20° C., in a weight proportion of 15:64:21 in a manner similar to Example 1. A hard capsule was prepared of this solution in the same manner as in Example 1 and the capsule was subjected to the disintegration test to give a result of the disintegration time of 6.0 minutes.

EXAMPLE 4

An aqueous dipping bath containing 12% by weight of solid matter was prepared in a manner similar to Example 1 by dissolving in water the same HEC and PVA-C as used in Preliminary Test in a weight proportion of 95:5 followed by de-aeration under reduced pressure after standing overnight. A #3 hard capsule was shaped of this solution by dipping a mandrel pin heated in advance at 60° C. in this solution kept at 40° C. and withdrawing the pin out of the bath taking 45 seconds followed by drying of the same in a drying oven at 90° C. for 30 minutes. The disintegration time of this hard capsule was 6.7 minutes as determined in the same manner as in Example 1.

EXAMPLE 5

An aqueous dipping bath containing 18% by weight of solid matter composed of the same HPMC and PVA-A as used in Preliminary Test described above and titanium dioxide pigment was prepared by mixing an aqueous solution of 95 parts by weight of the HPMC and 5 parts by weight of the polyvinyl alcohol in an overall concentration of 18.1% by weight with an aqueous dispersion of 2 parts by weight of the pigment in a small volume of water followed by deaeration under reduced pressure after standing overnight. A hard capsule containing the shading pigment was prepared of this dipping solution in the same manner as in Example 1 and subjected to the disintegration test to give a result of 5.8 minutes of the disintegration time.

EXAMPLE 6

The hard capsules shaped of the polymer blend of a cellulose ether and a polyvinyl alcohol prepared in Example 1, 2 and 3 and a commercially available gelatin-made capsule were each filled with vitamin C beads for direct tabletting and kept standing at a temperature of 40° C. under a relative humidity of 75% to examine the changes caused in the appearance of the capsules in the lapse of time. The results were that yellowing took place in the gelatin-made capsule already after three days of standing while no change was noticeable in each of the capsules made of the polymer blends of the cellulose ether and polyvinyl alcohol.

What is claimed is:

1. A hard capsule for medicinal use shaped from a mixture comprising from 70 to 98 parts by weight of a cellulose ether, of which the ether-forming substituent groups are selected from the group consisting of methyl, ethyl, hydroxyethyl and hydroxypropyl, and from 30 to 2 parts by weight of a polyvinyl alcohol.

2. The hard capsule for medicinal use as claimed in claim 1 wherein the cellulose ether is selected from the class consisting of methyl cellulose, hydroxyethyl cellulose, hydroxypropyl cellulose, hydroxyethyl methyl cellulose, hydroxyethyl ethyl cellulose and hydroxypropyl methyl cellulose.

3. The hard capsule for medicinal use as claimed in claim 1 wherein the cellulose ether has a degree of substitution with the alkyl and hydroxyalkyl groups of at least 1.4 per glucose unit.

4. The hard capsule for medicinal use as claimed in claim 1 wherein the cellulose ether has such a degree of polymerization that a 2% by weight aqueous solution thereof has a viscosity in the range from 2 to 15 centipoise at 20° C..

5. The hard capsule for medicinal use as claimed in claim 1 wherein the polyvinyl alcohol has a degree of saponification of at least 75% by moles.

6. The hard capsule for medicinal use as claimed in claim 1 wherein the polyvinyl alcohol has such a degree of polymerization that a 4% by weight aqueous solution thereof has a viscosity in the range from 3 to 80 centipoise at 20° C.

7. A method for the preparation of a hard capsule for medicinal use which comprises the steps of:

(a) dipping a mandrel pin of a capsule form in an aqueous solution containing from 70 to 98 parts by weight of a cellulose ether, of which the ether-forming substituent groups are selected from the class consisting of alkyl groups and hydroxyalkyl groups, and from 30 to 2 parts by weight of a polyvinyl alcohol dissolved therein;

(b) withdrawing the mandrel pin out of the aqueous solution with a layer of the aqueous solution adhering on the surface thereof;

(c) drying the aqueous solution adhering on the surface of the mandrel pin to form a capsule-shaped crust-like film of the polymeric blend composed of the cellulose ether and the polyvinyl alcohol; and (d) removing the mandrel pin out of the capsule-shaped crust-like film of the polymeric blend.

8. The method for the preparation of a hard capsule for medicinal use as claimed in claim 7 wherein the aqueous solution contains from 10 to 30% by weight of the cellulose ether and the polyvinyl alcohol as a total.

9. The method for the preparation of a hard capsule for medicinal use as claimed in claim 7 wherein the aqueous solution has a viscosity in the range from 1000 to 10000 centipoise at 20° C.

10. The method for the preparation of a hard capsule for medicinal use as claimed in claim 7 wherein the mandrel pin is preheated at a temperature in the range from 45 to 100° C. prior to dipping in the aqueous solution.

* * * * *